United States Patent
Cowan et al.

(10) Patent No.: US 11,364,130 B2
(45) Date of Patent: Jun. 21, 2022

(54) SPINAL IMPLANT SYSTEM AND METHOD

(71) Applicant: WARSAW ORTHOPEDIC INC., Warsaw, IN (US)

(72) Inventors: Benjamin D. Cowan, Memphis, TN (US); Cristian A. Capote, Memphis, TN (US); Adriaan J. Kuyler, Saint Augustine, FL (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 17/009,052

(22) Filed: Sep. 1, 2020

(65) Prior Publication Data

US 2022/0062006 A1 Mar. 3, 2022

(51) Int. Cl.
| | |
|---|---|
| *A61B 17/70* | (2006.01) |
| *A61F 2/46* | (2006.01) |
| *A61B 34/20* | (2016.01) |
| *A61F 2/30* | (2006.01) |
| *A61B 90/00* | (2016.01) |

(52) U.S. Cl.
CPC ............ *A61F 2/4611* (2013.01); *A61B 34/20* (2016.02); *A61B 2034/2051* (2016.02); *A61B 2034/2055* (2016.02); *A61B 2034/2063* (2016.02); *A61B 2034/2072* (2016.02); *A61B 2090/3764* (2016.02); *A61F 2002/3008* (2013.01); *A61F 2310/00023* (2013.01)

(58) Field of Classification Search
CPC ........ A61F 2/46; A61F 2/4611; A61F 2/4603; A61F 2002/4625–4629; A61B 2034/2046; A61B 2034/2051; A61B 2034/2074

See application file for complete search history.

(56) References Cited

U.S. PATENT DOCUMENTS

| | | | |
|---|---|---|---|
| 6,021,343 | A | 2/2000 | Foley et al. |
| 6,174,311 | B1 | 1/2001 | Branch et al. |
| 6,530,955 | B2 | 3/2003 | Boyle et al. |
| 7,575,580 | B2 | 8/2009 | Lim et al. |

(Continued)

FOREIGN PATENT DOCUMENTS

EP 3470022 A1 4/2019

OTHER PUBLICATIONS

International Search Report and Written Opinion dated Mar. 1, 2022, issued by the International Searching Authority (ISA/EPO) in International PCT Application No. PCT/US2021/048462 filed Aug. 31, 2021.

*Primary Examiner* — Eduardo C Robert
*Assistant Examiner* — Michelle C Eckman
(74) *Attorney, Agent, or Firm* — Sorell, Lenna & Schmidt, LLP

(57) ABSTRACT

An instrument includes a sleeve extending between proximal and distal ends. The sleeve defines a passageway. The proximal end includes an aperture extending into an outer surface of the sleeve. The distal end includes an engagement surface and an opening extending through the engagement surface. The opening is in communication with the passageway. A member is movably disposed in the aperture. The member includes a spring and a body. The body defines a bore. A shaft extends between opposite proximal and distal ends. The proximal end of the shaft extends through the bore. The distal end of the shaft extends through the opening. Systems and methods of use are disclosed.

20 Claims, 8 Drawing Sheets

(56) References Cited

U.S. PATENT DOCUMENTS

| | | | |
|---|---|---|---|
| 8,118,872 B2 | 2/2012 | Trudeau et al. | |
| 8,808,305 B2 | 8/2014 | Kleiner | |
| 8,998,924 B2 | 4/2015 | Simpson et al. | |
| 9,095,385 B2 | 8/2015 | Wallenstein et al. | |
| 9,439,782 B2 | 9/2016 | Kleiner | |
| 9,956,087 B2 | 5/2018 | Seifert et al. | |
| 9,987,144 B2 | 6/2018 | Seifert et al. | |
| 10,004,609 B2 | 6/2018 | Palmatier et al. | |
| 10,123,826 B2 | 11/2018 | Harper | |
| 10,285,715 B2 | 5/2019 | Peters et al. | |
| 10,292,836 B2 | 5/2019 | Josse et al. | |
| 10,342,677 B2 | 7/2019 | Ries | |
| 2005/0203538 A1 | 9/2005 | Lo et al. | |
| 2006/0095043 A1 | 5/2006 | Martz et al. | |
| 2006/0229729 A1 | 10/2006 | Gordon | |
| 2006/0235426 A1 | 10/2006 | Lim et al. | |
| 2006/0247655 A1 | 11/2006 | Francis et al. | |
| 2007/0093850 A1 | 4/2007 | Harris et al. | |
| 2007/0093897 A1 | 4/2007 | Gerbec et al. | |
| 2007/0142843 A1 | 6/2007 | Dye | |
| 2007/0162128 A1 | 7/2007 | DeRidder et al. | |
| 2007/0225726 A1 | 9/2007 | Dye et al. | |
| 2012/0296171 A1 | 11/2012 | Lovell et al. | |
| 2013/0282018 A1 | 10/2013 | Deridder et al. | |
| 2014/0172103 A1 | 6/2014 | O'Neil et al. | |
| 2015/0105833 A1 | 4/2015 | Simpson et al. | |
| 2015/0257769 A1 | 9/2015 | Papenfuss | |
| 2016/0220386 A9 | 8/2016 | Harris et al. | |
| 2018/0110629 A1 | 4/2018 | Ewer et al. | |
| 2018/0311051 A1* | 11/2018 | Donaldson | A61F 2/4611 |
| 2019/0021716 A1 | 1/2019 | Waugh et al. | |
| 2019/0274845 A1* | 9/2019 | Ludwig | A61F 2/4611 |
| 2019/0374350 A1* | 12/2019 | Milz | B25B 23/1427 |
| 2020/0253622 A1 | 8/2020 | Ries et al. | |
| 2020/0337860 A1* | 10/2020 | Kuyler | A61F 2/4455 |
| 2020/0405502 A1* | 12/2020 | Gephart | A61F 2/4455 |
| 2021/0059839 A1* | 3/2021 | Hessler | A61F 2/4611 |

\* cited by examiner

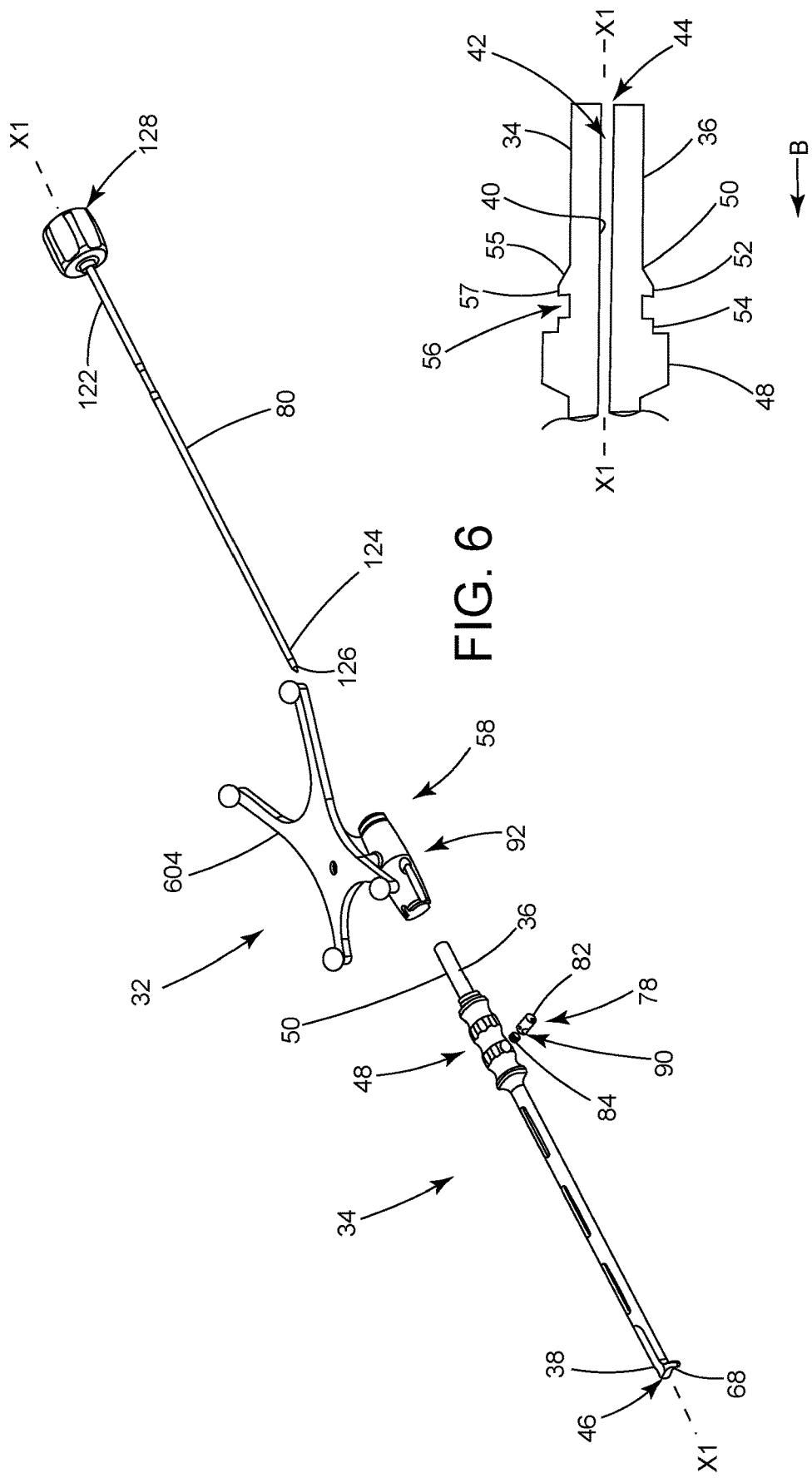

US 11,364,130 B2

SPINAL IMPLANT SYSTEM AND METHOD

TECHNICAL FIELD

The present disclosure generally relates to medical devices for the treatment of musculoskeletal disorders, and more particularly to a spinal implant system including an implant and an instrument configured to deliver the implant during a surgical procedure.

BACKGROUND

Spinal pathologies and disorders such as scoliosis and other curvature abnormalities, kyphosis, degenerative disc disease, disc herniation, osteoporosis, spondylolisthesis, stenosis, tumor and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs, such as, for example, bone fasteners, plates and interbody devices can be used to provide stability to a treated region. For example, during surgical treatment, interbody implants can be delivered to a surgical site for fixation with bone to immobilize a joint. The bone fasteners extend through a plate and/or an interbody device and into bone to fix at least a portion of the plate and/or the interbody device to the bone. This disclosure describes an improvement over these prior art technologies.

SUMMARY

In one embodiment, in accordance with the principles of the present disclosure, a surgical instrument comprises a sleeve extending along a longitudinal axis between opposite proximal and distal ends. An inner surface of the sleeve defines a passageway. The proximal end comprises an aperture extending through an outer surface of the sleeve. The distal end comprises an engagement surface and an opening extending through the engagement surface. The opening is in communication with the passageway. A member is movably disposed in the aperture. The member comprises a spring and a body. The body defines a bore. A shaft extends between opposite proximal and distal ends. The proximal end of the shaft extends through the bore. The distal end of the shaft extends through the opening.

In one embodiment, in accordance with the principles of the present disclosure, a surgical instrument comprises a sleeve extending between opposite proximal and distal ends. The sleeve comprises an inner surface defining a passageway. A part is coupled to the proximal end of the sleeve. The part comprises a plurality of first holes and an inner surface defining a channel. A shaft extends between opposite proximal and distal ends. The distal end of the shaft is positioned in the passageway and the channel. A knob is coupled to the proximal end of the shaft. The knob comprises a hub having a plurality of second holes. The knob comprises an insert disposed in the hub and a plurality of extensions positioned between the insert and the hub. The knob is rotatable between a first configuration in which the extensions are spaced apart from the first holes and a second configuration in which the extensions are disposed in the first holes. The knob is rotatable relative to the part when the knob is in the first configuration. The knob resists rotation relative to the part when the knob is in the second configuration.

In one embodiment, in accordance with the principles of the present disclosure, a surgical instrument comprises a sleeve extending along a first longitudinal axis between opposite proximal and distal ends. The sleeve comprises a first inner surface defining a passageway. The proximal end comprises an aperture extending into an outer surface of the sleeve and a second inner surface of the sleeve that is positioned between the first inner surface and the outer surface. The distal end comprises an engagement surface and an opening extending through the engagement surface. The opening is in communication with the passageway. The distal end comprising a peg extending outwardly from the engagement surface. The sleeve comprises a circumferential flange. An emitter is configured to generate a signal representative of the position of the surgical instrument. The emitter is coupled to the proximal end of the sleeve. The emitter comprises a plurality of first holes and an inner surface defining a channel. The emitter comprises a body and a pair of arms that are pivotable relative to the body and configured to engage the flange to couple the emitter to the sleeve. A member is movably disposed in the aperture. The member comprises a spring and a cylindrical body. The cylindrical body defines a bore. The spring comprises a first end that directly engages the second inner surface and an opposite second end that directly engages the cylindrical body. A shaft extends along a second longitudinal axis between opposite proximal and distal ends. The proximal end of the shaft extends through the bore and the channel. The distal end of the shaft extends through the opening. A knob is coupled to the proximal end of the shaft. The knob comprises a hub having a plurality of second holes. The knob comprises an insert disposed in the hub and a plurality of extensions positioned between the insert and the hub. The knob comprises a plurality of springs that are each positioned between the insert and one of the extensions. The hub comprises a threaded inner surface that directly engages a threaded outer surface of the insert to couple the insert to the hub. The member is configured to move the shaft relative to the sleeve between a first orientation in which the second longitudinal axis is coaxial with the first longitudinal axis and a second orientation in which the second longitudinal axis is offset from the first longitudinal axis. The knob is rotatable between a first configuration in which the extensions are spaced apart from the first holes and a second configuration in which the extensions are disposed in the first holes. The knob is rotatable relative to the emitter when the knob is in the first configuration. The knob resists rotation relative to the emitter when the knob is in the second configuration.

BRIEF DESCRIPTION OF THE DRAWINGS

The present disclosure will become more readily apparent from the specific description accompanied by the following drawings, in which:

FIG. 6 is a perspective view of components of the surgical instrument shown in FIG. 1, with parts separated;

FIG. 7 is an enlarged side, cross-sectional, breakaway view of a component of the surgical instrument shown in FIG. 1 taken at Detail A in FIG. 6;

Like reference numerals indicate similar parts throughout the figures.

DETAILED DESCRIPTION

Figure 1:
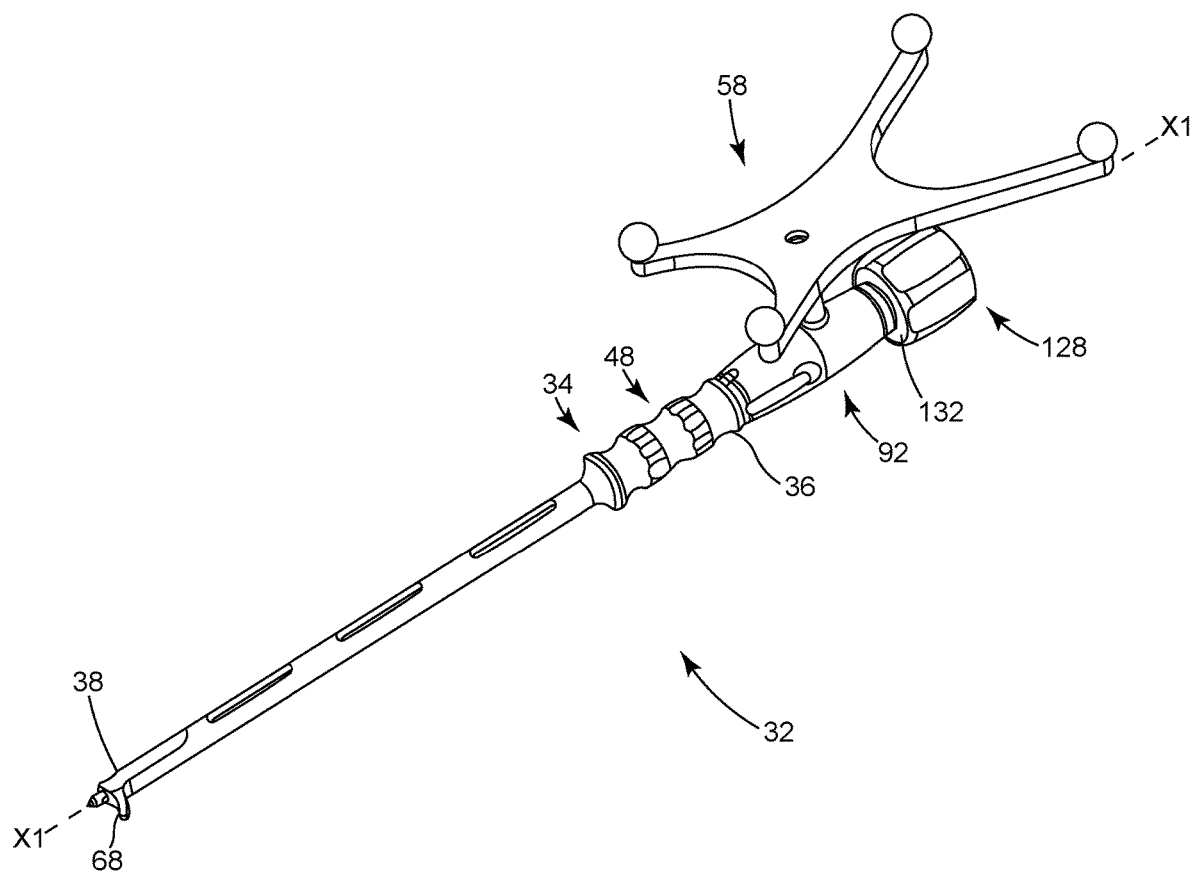
FIG. 1 is a perspective view of components of a surgical instrument, in accordance with the principles of the present disclosure.
Figure 2:
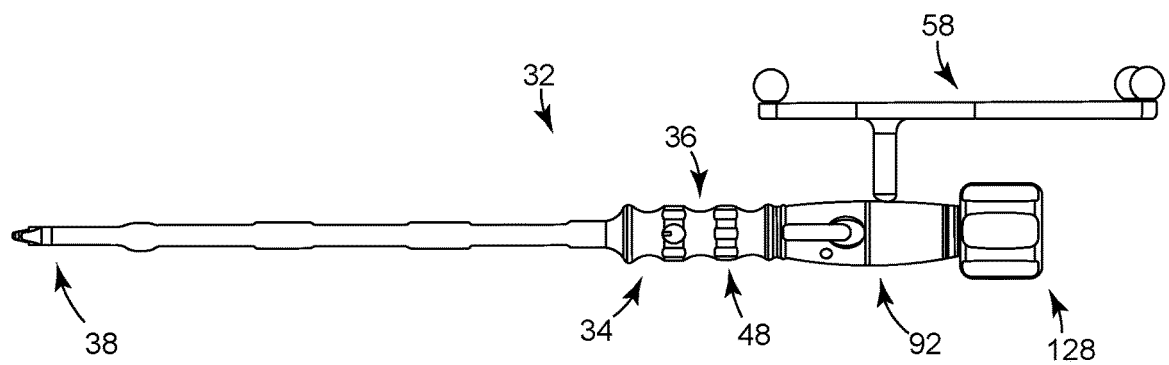
FIG. 2 is a side view of components of the surgical instrument shown in FIG. 1.

The exemplary embodiments of the spinal system and related methods of use disclosed are discussed in terms of medical devices for the treatment of musculoskeletal disorders and more particularly, in terms of a surgical system and a method for treating a spine. In some embodiments, the systems and methods of the present disclosure comprise medical devices including surgical instruments and implants that are employed with a surgical treatment, as described herein, for example, with a cervical, thoracic, lumbar and/or sacral region of a spine.

In some embodiments, the present surgical system includes instrumentation that utilizes navigation assisted technology. The instrumentation of the present surgical system utilizes one or more trackers that can be removed from such instrumentation, while still allowing at least two features that are preferable on a non-navigated (standard) inserter instrument. The first feature is a safety catch for the inner shaft so that it cannot freely fall out of the inserter and become damaged or lose sterility, as discussed herein. The second feature is a novel ratchet lock that works with holes in the proximal end of the tracker, such as, for example, a NAVLOCK™ tracker sold by Medtronic Navigation, Inc. of Louisville, Colo., to aid in the locking of the inner shaft to the inserter and prevent backout during use, as discussed herein. While a NAVLOCK™ compatible instrument is much more cost effective to make than an integrated tracker, NAVLOCK™ compatibility often requires sacrifices to functionality of the instrument. The current disclosure allows for NAVLOCK™ compatibility with all of the same functionality as non-navigated (standard) instrumentation.

In some embodiments, the surgical system of the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the surgical system of the present disclosure may be employed with other osteal and bone related applications, including those associated with diagnostics and therapeutics. In some embodiments, the disclosed surgical system may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The surgical system of the present disclosure may also be alternatively employed with procedures for treating the lumbar, cervical, thoracic, sacral and pelvic regions of a spinal column. The surgical system of the present disclosure may also be used on animals, bone models and other non-living substrates, such as, for example, in training, testing and demonstration.

The surgical system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. In some embodiments, as used in the specification and including the appended claims, the term "tissue" includes soft tissue, ligaments, tendons, cartilage and/or bone unless specifically referred to otherwise.

The following discussion includes a description of a surgical system including implants, related components and methods of employing the surgical system in accordance with the principles of the present disclosure. Alternate embodiments are also disclosed. Reference is made in detail to the exemplary embodiments of a surgical system 30, which are illustrated in the accompanying figures.

The components of surgical system 30 can be fabricated from biologically acceptable materials suitable for medical applications, including metals, synthetic polymers, ceramics and bone material and/or their composites. For example, the components of surgical system 30, individually or collectively, can be fabricated from materials such as stainless steel alloys, aluminum, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of surgical system 30 may have material composites, including the above materials, to achieve various desired characteristics such as strength, rigidity, elasticity, compliance, biomechanical performance, durability and radiolucency or imaging preference. The components of surgical system 30, individually or collectively, may also be fabricated from a heterogeneous material such as a combination of two or more of the above-described materials. The components of surgical system 30 may be monolithically formed, integrally connected or include fastening elements and/or instruments, as described herein.

Surgical system 30 is employed, for example, with a fully open surgical procedure, a minimally invasive procedure including percutaneous techniques, and mini-open surgical techniques to deliver and introduce instrumentation and/or one or more spinal implants, such as, for example, one or more components of a bone fastener, at a surgical site of a patient, which includes, for example, a spine. In some embodiments, the spinal implant can include one or more components of one or more spinal constructs, such as, for example, interbody devices, interbody cages, bone fasteners, spinal rods, tethers, connectors, plates and/or bone graft, and can be employed with various surgical procedures including surgical treatment of a cervical, thoracic, lumbar and/or sacral region of a spine.

Figure 3:
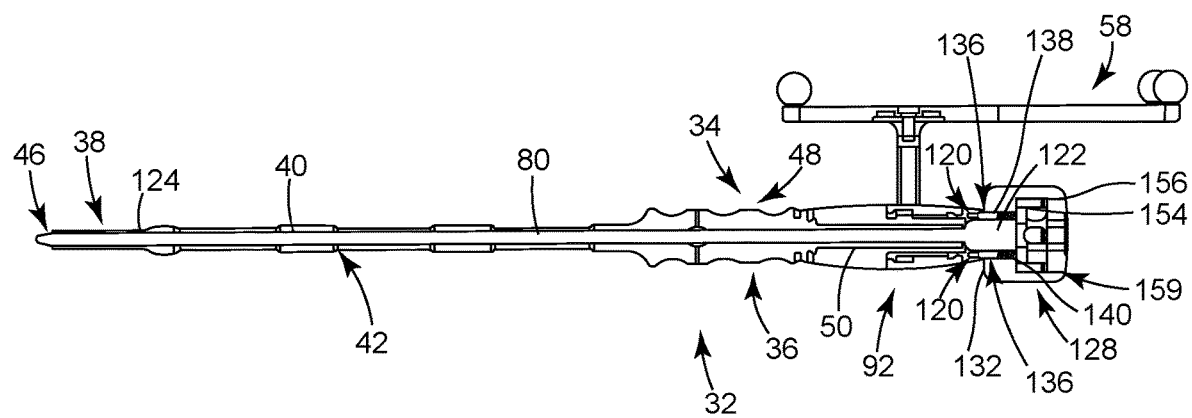
FIG. 3 is a side, cross-sectional view of components of the surgical instrument shown in FIG. 1.
Figure 4:
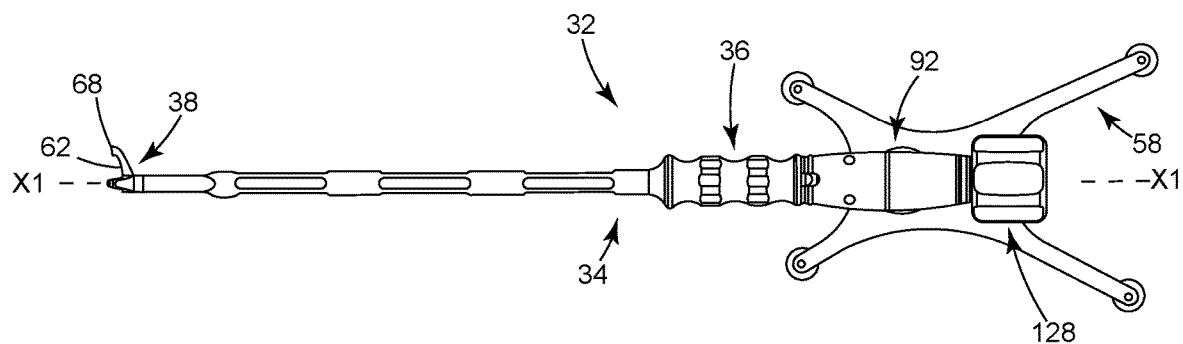
FIG. 4 is a bottom view of components of the surgical instrument shown in FIG. 1.
Figure 5:
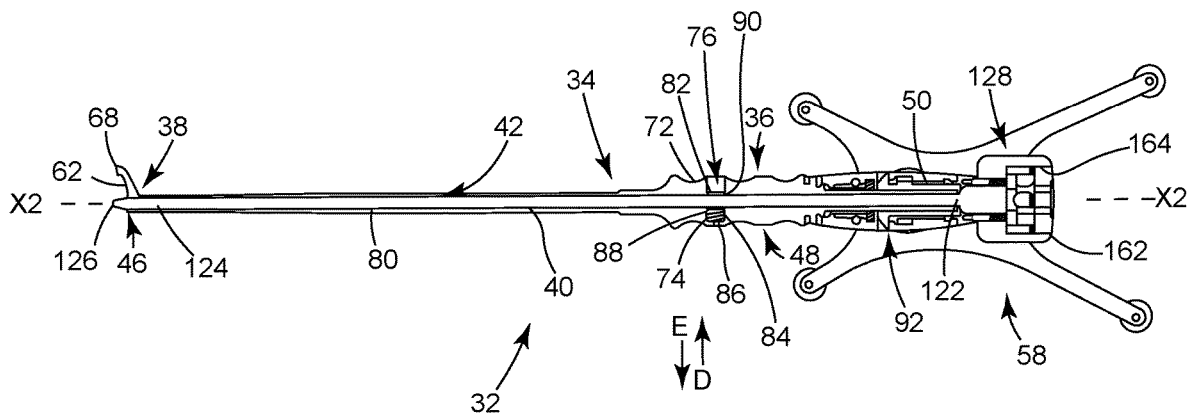
FIG. 5 is a bottom, cross-sectional view of components of the surgical instrument shown in FIG. 1.
Figure 8:
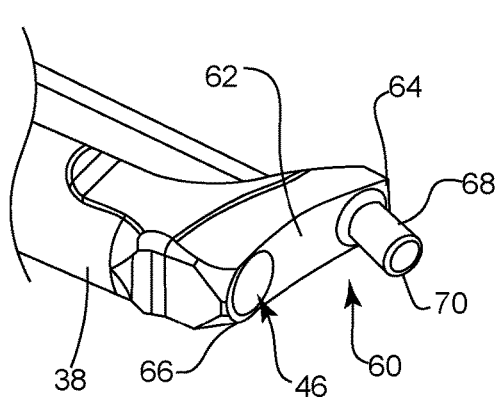
FIG. 8 is a perspective, breakaway view of one embodiment of a component of the surgical instrument shown in FIG. 1, in accordance with the principles of the present disclosure.
Figure 9:
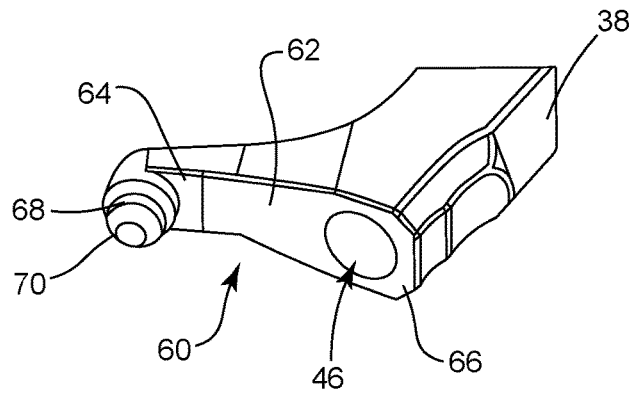
FIG. 9 is a perspective, breakaway view of one embodiment of a component of the surgical instrument shown in FIG. 1, in accordance with the principles of the present disclosure.

Surgical system 30 includes a surgical instrument 32 configured to selectively deliver one or more implants to a surgical site, such as, for example, an intervertebral space defined by adjacent vertebrae, as discussed herein. Instrument 32 includes an inserter, such as, for example, a sleeve 34 extending along a longitudinal axis X1 between a proximal end 36 and an opposite distal end 38. An inner surface, such as, for example, a first inner surface 40 of sleeve 34 defines a passageway 42. Passageway 42 is coaxial with axis X1. End 36 includes an opening 44 that is in communication with passageway 42, as best shown in FIG. 7. End 38 includes an opening 46 that is in communication with passageway 42, as best shown in FIGS. 3, 5 and 6. In some embodiments, opening 44 is coaxial with opening 46. In some embodiments, openings 44, 46 are coaxial with axis X1. In some embodiments, opening 44 has a diameter that is equal to the diameter of opening 46. In some embodiments, openings 44, 46 each have a diameter that is equal to the diameter of passageway 42. In some embodiments, passageway 42 has a uniform diameter along an entire length of passageway 42. In some embodiments, passageway 42, opening 44 and/or opening 46 may be variously shaped, such as, for example, circular, oval, oblong, triangular, square, polygonal, irregular, uniform, non-uniform, offset, staggered, undulating, arcuate, variable and/or tapered. In some embodiments, passageway 42, opening 44 and/or opening 46 may be disposed at alternate orientations, relative to axis X1, such as, for example, transverse, perpendicular and/or other angular orientations such as acute or obtuse, co-axial and/or may be offset or staggered. In some embodiments, sleeve 34 is monolithically and/or integrally formed to provide strength and/or rigidity to sleeve 34.

End 36 includes a gripping portion 48 and a cylindrical tube 50 that extends proximally from gripping portion 48. A proximal end of tube 50 defines opening 44, as shown in FIG. 7. Gripping portion 48 includes gripping features, such as, for example, indentations and/or protrusions configured to facilitate gripping by hand. End 36 includes circumferential flanges 52, 54 extending outwardly from tube 50 such that flange 52 is spaced apart from flange 54 by a recess 56, as best shown in FIG. 7. Flanges 52, 54 each extend 360 degrees about axis X1. Flanges 52, 54 and recess 56 are configured to connect sleeve 34 with a part, such as, for example, an emitter 58 configured to generate a signal representative of a position of instrument 32, as discussed herein. In some embodiments, flange 52 includes a ramp surface 55 and a horizontal surface 37 that extends from surface 55. Surface 55 extends at an acute angle relative to axis X1 and surface 57 extends parallel to axis X1. Surfaces 55, 57 allow emitter 58 to be translated along tube 50 in the direction shown by arrow B in FIG. 7 such that a surface of emitter 58 rides along surfaces 55, 57 for disposal of at least a portion of emitter 58 in recess 56 to connect emitter 58 with sleeve 34, as discussed herein.

End 38 defines an engagement portion 60 configured to directly engage one or more surfaces of an implant, such as, for example, an interbody implant to couple the implant to instrument 32, as discussed herein. Engagement portion 60 comprises an engagement surface 62 extending from an end 64 to an opposite end 66. In some embodiments, engagement portion 60 comprises a peg 68 extending outwardly from surface 62 at end 64 and opening 46 extends through end 66. In some embodiments, engagement portion 60 does not include a peg or any other structure extending from engagement surface 62 and engagement portion 60 includes only opening 46, wherein opening 46 can be variously positioned relative to engagement surface 62. Peg 68 is permanently fixed relative to surface 62. In some embodiments, opening 46 is coaxial with passageway 42 and axis X1 and peg 68 extends at an acute angle relative to axis X1. Peg 68 has a solid configuration that is free of any gaps or openings to provide strength and rigidity to peg 68. In some embodiments, peg 68 has a beveled tip 70 to facilitate insertion of peg 68 into a cavity of an implant, for example, to couple instrument 32 to the implant, as discussed herein. In some embodiments, the beveled tip is biased toward one side. In some embodiments, peg 68 is cone shaped. In some embodiments, peg 68 is cylindrical. In some embodiments, peg 68 is variously shaped, such as, for example, oval, oblong, triangular, square, polygonal, irregular, uniform, non-uniform, offset, staggered, undulating, arcuate, variable and/or tapered.

Sleeve 34 includes an outer surface 72 opposite surface 40 and an inner surface, such as, for example, a second inner surface 74 positioned between surface 40 and surface 72. Sleeve 34 includes an aperture 76 that extends through surfaces 40, 72 and into surface 74, as best shown in FIG. 5. Aperture 76 extends perpendicular to axis X1 and is configured for disposal of a member, such as, for example, a safety catch 78 to prevent a shaft 80 from falling out of passageway 42, as discussed herein. Catch 78 comprises a cylindrical body 82 and a biasing element, such as, for example, a spring 84. Body 82 and spring 84 are positioned within aperture 76 such that an end 86 of spring 84 directly engages surface 74 and an opposite end 88 of spring 84 directly engages body 82 to bias body 82 away from surface 74. Body 82 includes a bore 90 that extends completely through a thickness of body 82. Bore 90 is configured for disposal of shaft 80, as discussed herein. In some embodiments, shaft 80 and bore 90 have different cross-sectional shapes. In some embodiments, shaft 80 and bore 90 have the same cross-sectional shape, such as, for example, circular, and bore 90 has a diameter that is greater than a diameter of shaft 80 to allow shaft 80 to be positioned within bore 90. In some embodiments, the diameter of bore 90 is only slightly greater than the diameter of shaft 80 such that shaft 80 is unable to translate relative to body 82 in the direction shown by arrow D in FIG. 5 or the direction shown by arrow E in FIG. 5 when shaft 80 is disposed in bore 90. In some embodiments, shaft 80 and/or bore 90 may have various cross section configurations, such as, for example, circular, oval, oblong, triangular, rectangular, square, polygonal, irregular, uniform, non-uniform, variable, tubular and/or tapered.

Figure 10:
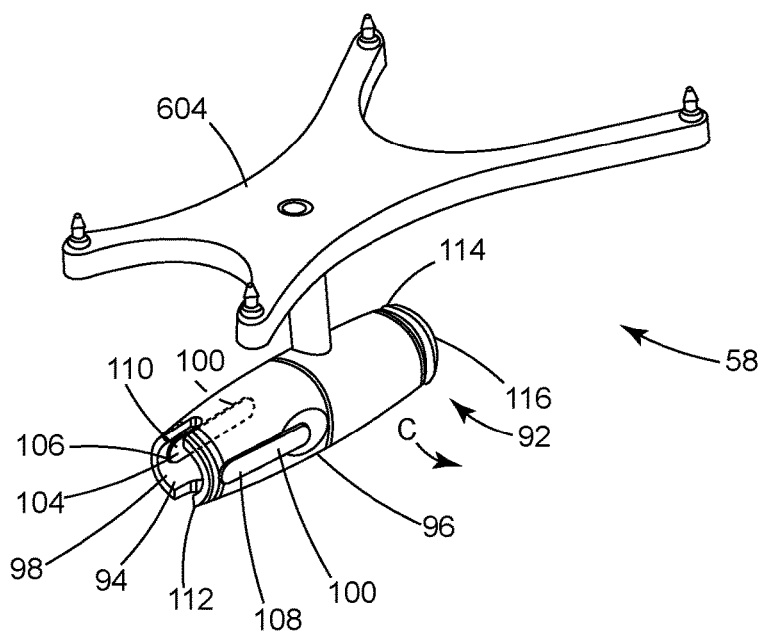
FIG. 10 is a perspective view of a component of the surgical instrument shown in FIG. 1.

Emitter 58 includes a collar 92 having an inner surface 94 and an outer surface 96, as best shown in FIG. 10. Surface 94 defines a channel, such as, for example, a passageway 98. Surface 94 is configured for releasable engagement with sleeve 34. Passageway 98 is configured to receive tube 50 and at least one of flanges 52, 54. Surface 94 defines a lock, such as, for example, at least one resilient prong or tab 100. In one embodiment, collar 92 includes a plurality of tabs 100, as shown in FIG. 10. Each tab 100 includes an inner surface 104 that defines a cutout 106 and an outer surface 108. Each cutout 106 includes raised portions 110 that define edges of cutout 106. Cutout 106 is configured to receive flange 52. In its initial position, surface 108 is aligned with surface 96 of collar 92.

Emitter 58 is connected with sleeve 34 by translating emitter 58 translated over tube 50, in the direction shown by arrow B in FIG. 7, such that flange 52 engages portions 110 and applies a force to tabs 100 to move tabs 100 outwardly, in the direction shown by arrows C in FIG. 10, such that surface 108 is deflected from surface 96. As flange 52 translates over portions 110, flange 52 move into cutouts 106 allowing tabs 100 to move back to their initial position. In some embodiments, emitter 58 is configured for removable engagement with sleeve 34. In some embodiments, emitter 58 may be integrally formed with sleeve 34. In one embodiment, flange 54 is configured to engage collar 92 to reduce vibrations resulting from the torque of an actuator. In some embodiments, sleeve 34 does not include any retention features and instead rely on the lock defined by tabs 100 to maintain the connection between emitter 58 and sleeve 34.

Figures 13, 14, 15:
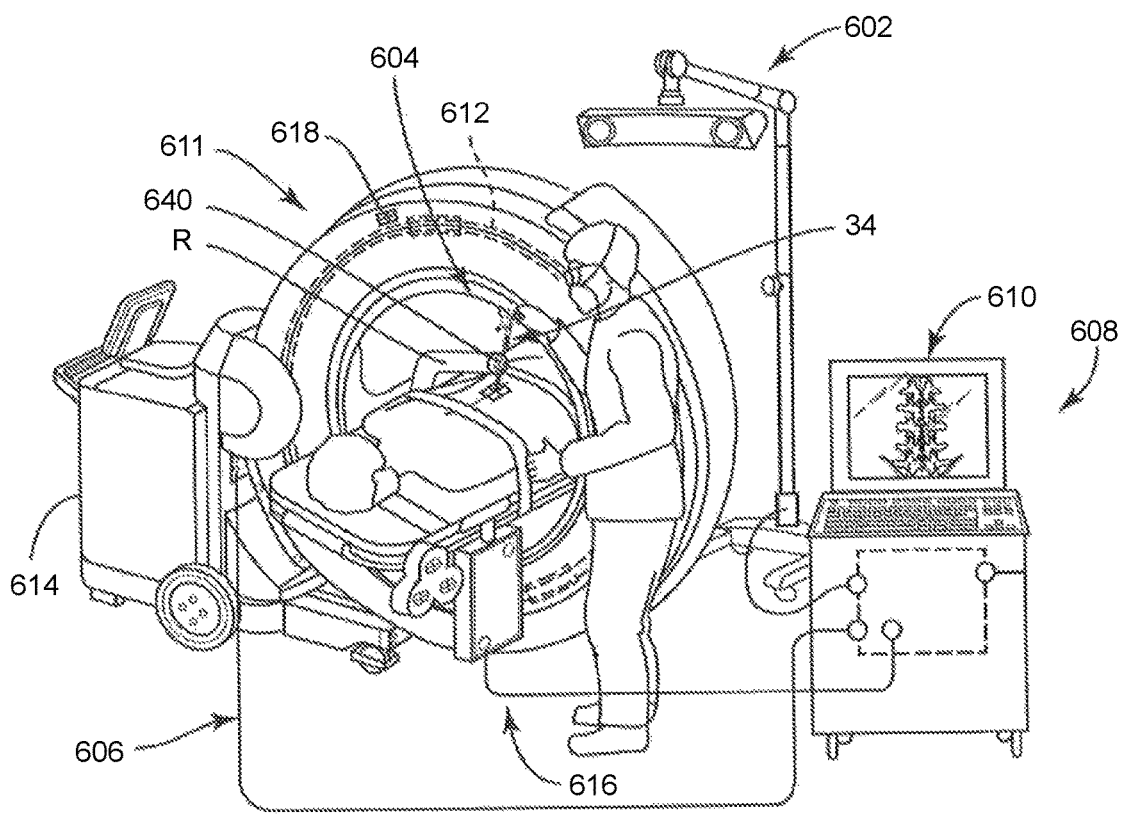
FIG. 13 is a perspective view of components of one embodiment of a surgical system in accordance with the principles of the present disclosure.
FIG. 14 is a perspective, cross-sectional, breakaway view of one embodiment of a surgical system in accordance with the principles of the present disclosure.
FIG. 15 is a perspective, cross-sectional, breakaway view of one embodiment of a surgical system in accordance with the principles of the present disclosure.

Sleeve 34 is configured for disposal adjacent a surgical site such that emitter 58 is oriented relative to a sensor array 602 to facilitate communication between emitter 58 and sensor array 602 during a surgical procedure, as shown in FIG. 13. Emitter 58 is configured to generate a signal representative of a position of instrument 32 relative to tissue. In some embodiments, the image guide may include human readable visual indicia, human readable tactile indicia, human readable audible indicia, one or more components having markers for identification under x-ray, fluoroscopy, CT or other imaging techniques, at least one light emitting diode, a wireless component, a wired component, a near field communication component and/or one or more components that generate acoustic signals, magnetic signals, electromagnetic signals and/or radiologic signals.

Figure 12:
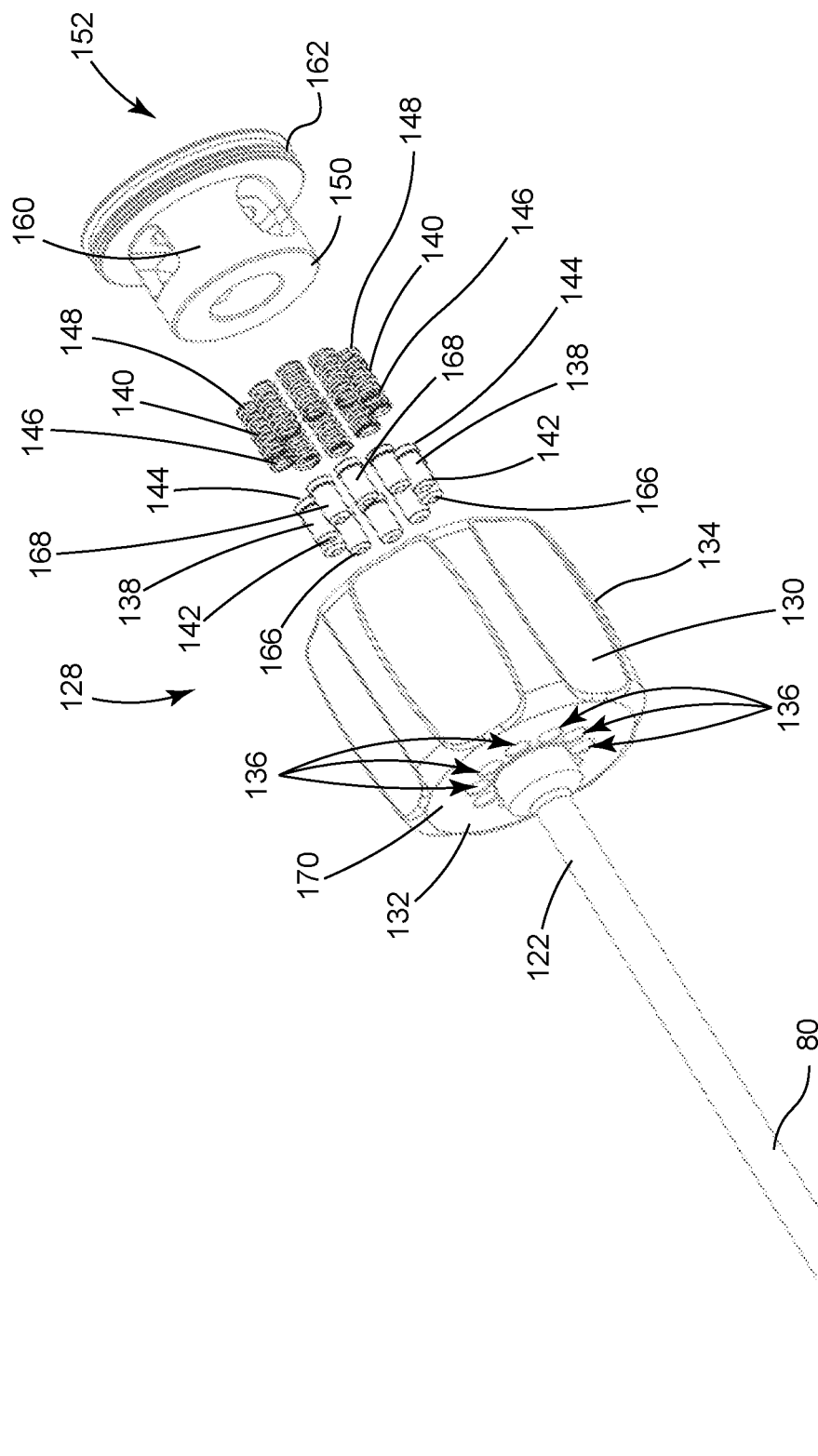
FIG. 12 is a perspective view of components of the surgical instrument shown in FIG. 1, with parts separated.

Emitter 58 includes an emitter array 604, as shown in FIG. 10. Emitter array 604 is configured for generating a signal to sensor array 602 of a surgical navigation system 606, as shown in FIG. 12. In some embodiments, the signal generated by emitter array 604 represents a position of instrument 32 relative to tissue, such as, for example, bone. In some embodiments, the signal generated by emitter array 604 represents a three dimensional position of instrument 32 relative to tissue. In some embodiments, emitter array 604 includes a reflectance array and/or is configured to reflect a signal to sensor array 602.

In some embodiments, sensor array 602 receives signals from emitter array 604 to provide a three-dimensional spatial position and/or a trajectory of instrument 34 relative to tissue. Emitter array 604 communicates with a processor of a computer 608 of navigation system 606 to generate data for display of an image on a monitor 610. In some embodiments, sensor array 602 receives signals from emitter array 604 to provide a visual representation of a position of instrument 32 relative to tissue. See, for example, similar surgical navigation components and their use as described in U.S. Pat. Nos. 6,021,343, 6,725,080, 6,796,988, the entire contents of each of these references being incorporated by reference herein.

Surgical navigation system 606 is configured for acquiring and displaying medical imaging, such as, for example, x-ray images appropriate for a given surgical procedure. In some embodiments, pre-acquired images of a patient are collected. In some embodiments, surgical navigation system 606 can include an O-arm® imaging device 611 sold by Medtronic Navigation, Inc. having a place of business in Louisville, Colo., USA. Imaging device 611 may have a generally annular gantry housing that encloses an image capturing portion 612.

In some embodiments, navigation system 606 comprises an image capturing portion 614 that may include an x-ray source or emission portion and an x-ray receiving or image receiving portion located generally or as practically possible 180 degrees from each other and mounted on a rotor (not shown) relative to a track of image capturing portion 614. Image capturing portion 614 can be operable to rotate 360 degrees during image acquisition. Image capturing portion 614 may rotate around a central point or axis, allowing image data of the patient to be acquired from multiple directions or in multiple planes. Surgical navigation system 606 can include those disclosed in U.S. Pat. Nos. 8,842,893; 7,188,998; 7,108,421; 7,106,825; 7,001,045; and 6,940,941; the entire contents of each of these references being incorporated by reference herein.

In some embodiments, surgical navigation system 606 can include C-arm fluoroscopic imaging systems, which can generate three-dimensional views of a patient. The position of image capturing portion 614 can be precisely known relative to any other portion of an imaging device of navigation system 606. In some embodiments, a precise knowledge of the position of image capturing portion 614 can be used in conjunction with a tracking system 616 to determine the position of image capturing portion 614 and the image data relative to the patient.

Tracking system 616 can include various portions that are associated or included with surgical navigation system 606. In some embodiments, tracking system 616 can also include a plurality of types of tracking systems, such as, for example, an optical tracking system that includes an optical localizer, such as, for example, sensor array 602 and/or an EM tracking system that can include an EM localizer. Various tracking devices can be tracked with tracking system 616 and the information can be used by surgical navigation system 606 to allow for a display of a position of an item, such as, for example, a patient tracking device, an imaging device tracking device 618, and an instrument tracking device, such as, for example, emitter array 604, to allow selected portions to be tracked relative to one another with the appropriate tracking system.

In some embodiments, the EM tracking system can include the STEALTHSTATION® AXIEM™ Navigation System, sold by Medtronic Navigation, Inc. having a place of business in Louisville, Colo. Exemplary tracking systems are also disclosed in U.S. Pat. Nos. 8,057,407, 5,913,820, 5,592,939, the entire contents of each of these references being incorporated by reference herein.

Fluoroscopic images taken are transmitted a computer 614 where they may be forwarded to computer 608. Image transfer may be performed over a standard video connection or a digital link including wired and wireless. Computer 608 provides the ability to display, via monitor 610, as well as save, digitally manipulate, or print a hard copy of the received images. In some embodiments, images may also be displayed to the surgeon through a heads-up display.

In some embodiments, surgical navigation system 606 provides for real-time tracking of the position of instrument 34 relative to tissue can be tracked. Sensor array 602 is located in such a manner to provide a clear line of sight with emitter array 604, as described herein. In some embodiments, fiducial markers of emitter array 604 communicate with sensor array 602 via infrared technology. Sensor array 602 is coupled to computer 608, which may be programmed with software modules that analyze signals transmitted by sensor array 602 to determine the position of each object in a detector space.

In some embodiments, instrument 34 is configured for use with a guide member, such as, for example, an end effector 640 of a robotic arm R. End effector 640 defines a channel configured for passage of a bone fastener and disposal of instrument 34. Robotic arm R includes position sensors (not shown), similar to those referenced herein, which measure, sample, capture and/or identify positional data points of end effector 640 in three dimensional space for a guide-wireless insertion of instrument 34. In some embodiments, the position sensors of robotic arm R are employed in connection with surgical navigation system 606 to measure, sample, capture and/or identify positional data points of end effector 640 in connection with surgical treatment, as described herein. The position sensors are mounted with robotic arm R and calibrated to measure positional data points of end effector 640 in three dimensional space, which are communicated to computer 608.

Figure 11:
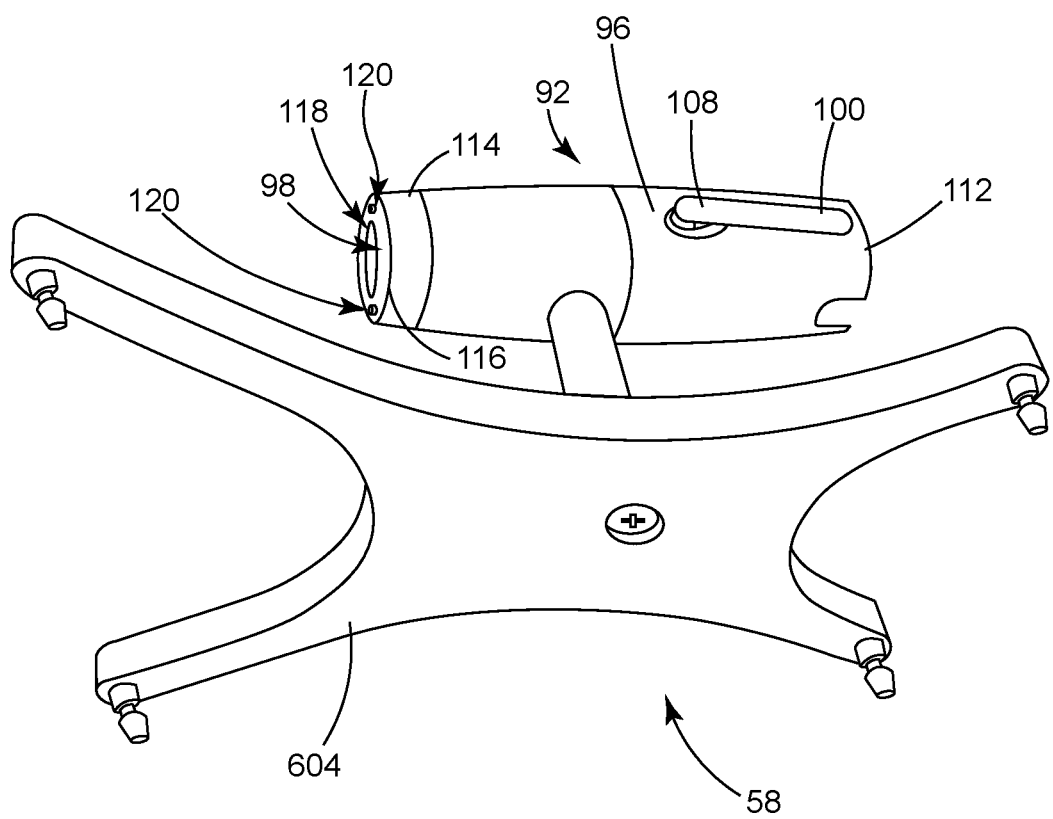
FIG. 11 is a perspective view of a component of the surgical instrument shown in FIG. 1.

Collar 92 comprises an end 112 that includes tabs 100 and an opposite end 114 having a wall 116. An opening 118 extends through wall 116 and is in communication with passageway 98. Wall 116 includes a plurality of spaced apart holes 120 disposed radially about opening 118, as best shown in FIG. 11. Holes 120 are configured for engagement with components of instrument 34 to aid in the locking of shaft 80 to sleeve 34 and prevent backout during use, as discussed herein. In some embodiments, holes 120 are beveled to facilitate insertion of components of instrument 34. In some embodiments, holes 120 extend parallel to axis X1 when emitter 58 is coupled to sleeve 34. In some embodiments, holes 120 may be disposed at alternate orientations, relative to axis X1, such as, for example, transverse and/or other angular orientations such as acute or obtuse, co-axial and/or may be offset or staggered. In some embodiments, holes 120 may have various cross section configurations, such as, for example, circular, oval, oblong, triangular, square, polygonal, irregular, uniform, non-uniform, offset, staggered, undulating, arcuate, variable and/or tapered.

Shaft 80 extends along a longitudinal axis X2 between a proximal end 122 and an opposite distal end 124 including a tip 126. Shaft 80 is rotatably positioned in passageway 42 such that shaft 80 extends through bore 90 of catch 78 and tip 126 extends through opening 46, as shown in FIG. 5. Catch 78 is configured to move shaft 80 relative to sleeve 34 between a first orientation in which the axis X2 is coaxial with axis X1 and a second orientation in which axis X2 is offset from axis X1. That is, axis X2 is not coaxial with axis X2 when shaft 80 is in the second orientation. When shaft 80 is in the first orientation, bore 90 is coaxial with axis X1 and shaft 80 is capable of freely falling out of passageway 42. As such, spring 84 biases shaft 80 to the second configuration, which positions bore 90 such that bore 90 is offset from axis X1 and shaft 80 is prevented from falling out of passageway 42. That is, as catch 78 moves shaft 80 from the first orientation to the second orientation, body 82 moves relative to sleeve 34 and shaft 80 in the direction shown by arrow D in FIG. 5. As, body 82 moves relative to sleeve 34 and shaft 80 in the direction shown by arrow D in FIG. 5, an inner surface of body 82 that defines bore 90 directly engages an outer surface of shaft 80 to move shaft 80 relative to sleeve 34 in the direction shown by arrow D in FIG. 5 to prevent shaft 80 from falling out of passageway 42. In some embodiments, shaft 80 may be moved from the second orientation to the first orientation by moving body 82 in the direction shown by arrow E in FIG. 5 to overcome the force provided by spring 84. In some embodiments, instrument 34 includes a button, such as, for example, a push button positioned in aperture 76 such that the button directly engages body 82 and is functional to overcome the force provided by spring 84 and move body 82 in the direction shown by arrow E in FIG. 5 to move shaft 80 from the second orientation to the first orientation. Because shaft 80 is biased to the second orientation by spring 84, body 82 will move in the direction shown by arrow D in FIG. 5 to move shaft from the first orientation to the second orientation once the button is released.

A knob 128 is coupled to end 122. Knob 128 includes a hub 130 coupled directly to end 122. In some embodiments, hub 130 is removable from end 122. In some embodiments, hub 130 is permanently fixed to end 122 such that hub 130 cannot be removed from end 122 without breaking hub 130 and/or end. In some embodiments, hub 130 is integrally and/or monolithically formed with end 122. Hub 130 includes a wall, such as, for example, a plate 132 and a side wall 134 extending from plate 132. Plate 132 extends perpendicular to axis X2 and includes a plurality of spaced apart holes 136 disposed radially about shaft 80, as best shown in FIG. 12. That is, holes 136 are disposed radially about axis X2 such that none of holes 136 is coaxial with axis X2. Side wall 134 extends parallel to axis X2 and includes gripping features, such as, for example, indentations and/or protrusions configured to facilitate gripping by hand. In some embodiments, plate 132 and/or side wall 134 may be disposed at alternate orientations, relative to axis A2, such as, for example, transverse, perpendicular and/or other angular orientations such as acute or obtuse, co-axial and/or may be offset or staggered. In some embodiments, shaft 80 is monolithically and/or integrally formed to provide strength and/or rigidity to shaft 80. In some embodiments, holes 136 are beveled to facilitate insertion of components of instrument 34. In some embodiments, holes 136 extend parallel to axis X2. In some embodiments, holes 136 may be disposed at alternate orientations, relative to axis X2, such as, for example, transverse and/or other angular orientations such as acute or obtuse, co-axial and/or may be offset or staggered. In some embodiments, holes 136 may have various cross section configurations, such as, for example, circular, oval, oblong, triangular, square, polygonal, irregular, uniform, non-uniform, offset, staggered, undulating, arcuate, variable and/or tapered. In some embodiments, holes 136 each have a diameter that is equal to the diameters of holes 120. In some embodiments, holes 136 each have a diameter that is greater to or less than the diameters of holes 120.

Knob 128 includes a plurality of extensions 138 and a plurality of springs 140. Extensions 138 and springs 140 are disposed radially about axis X2 such that none of extensions 138 or springs 140 is coaxial with axis X2. Extensions 138 each include an end 142 positioned in one of holes 136 and an opposite end 144. In some embodiments, ends 142 each include a tapered tip 166 configured to facilitate insertion of extensions 138 into holes 120, as discussed herein. Springs 140 each include an end 146 that directly engages one of ends 144 and an opposite end 148 that directly engages and end surface 150 of an insert 152 of knob 128. In particular, a proximal surface 154 of plate 134 and an inner surface 158 of side wall 156 define a cavity 159, as shown in FIG. 3, for example. Insert 152 is positioned in cavity 159 such that a side wall 160 of insert 152 engages surface 156 and springs 140 are each positioned between one of extensions 138 and surface 150. In some embodiments, insert 152 is permanently fixed relative to hub 130, such as, for example, by welding. In some embodiments, insert 152 is monolithically and/or integrally formed with hub 130. In some embodiments, insert 152 includes a threaded outer surface 152 that engages a threaded inner surface 164 of hub 130 to couple insert 152 to hub 130. In some embodiments, insert 152 can be variously connected with hub 130, such as, for example, monolithic, integral connection, frictional engagement, threaded engagement, mutual grooves, screws, adhesive, nails, barbs and/or raised element. In some embodiments, surface 150 may be disposed at alternate orientations, relative to axis X2, such as, for example, transverse, perpendicular and/or other angular orientations such as acute or obtuse, co-axial and/or may be offset or staggered.

Knob 128 is rotatable between a first configuration in which extensions 138 are spaced apart from holes 120 or only tips 166 of extensions 138 are positioned within holes 120 and a second configuration in which extensions 138 are disposed in holes 120. Knob 128 is rotatable relative to emitter 58 when knob 128 is in the first configuration. Knob 128 resists rotation relative to emitter 58 when knob 128 is in the second configuration. In some embodiments, knob 128 is prevented from rotating relative to emitter 58 when knob 128 is in the second configuration. In some embodiments, cylindrical portions 168 of extensions 138 are positioned in holes 120 when extensions 138 are fully disposed in the holes 120 and knob 128 is in the second configuration. In some embodiments, cylindrical portions 168 of extensions 138 are positioned in holes 136 and tips 166 of extensions 138 are positioned outside of holes 136 when knob 128 is in the first configuration and the second configuration.

Shaft 80 is rotatable relative to sleeve 34 when knob 128 is in the first configuration and shaft 80 is prevented from rotating relative to sleeve 34 when knob 128 is in the second configuration. Indeed, when only tips 166 of extensions 138 are positioned within holes 120, the tapered configuration of tips 166 allows tips 166 to move in and out of adjacent holes 120 as knob 128 is rotated relative to sleeve 34. When extensions 138 are inserted further into holes 120 such that cylindrical portions 168 of extensions 138 are positioned within holes 120, knob 128 Is prevented from being rotated relative to sleeve 34 since extensions 138 are prevented from moving from one of holes 120 to another one of holes 120. Knob 128 is biased to the second configuration by springs 140. That is, springs 140 move extensions 138 away from insert 152 such that extensions 138 move through holes 136 and into holes 120. In some embodiments, the force exerted by springs 140 to extensions 138 is sufficient to move knob 128 from the first configuration to the second configuration when holes 136 are each aligned with one of holes 120.

In some embodiments, insert 152 is fixed relative to hub 130 along axis X2 as knob 128 moves between the first configuration and the second configuration. That is, insert 152 does not move along axis X2 relative to hub 130 as knob 128 moves between the first configuration and the second configuration. In some embodiments, holes 136 are each offset from each of holes 120 when the knob 128 is in the first configuration and each of holes 136 is aligned with one of holes 120 when knob 128 is in the second configuration. That is, none of holes 136 is coaxial with any of holes 120 when the knob 128 is in the first configuration and each of holes 136 is coaxial with one of holes 120 when knob 128 is in the second configuration. In some embodiments, tips 166 of extensions 138 are flush with a distal surface 170 of plate 132 when knob 128 is in the first configuration and tips 166 of extensions 138 are distal to surface 170 when knob 128 is in the second configuration. In some embodiments, tips 166 of extensions 138 directly engage wall 166 between holes 120 when knob 128 is in the first configuration and tips 166 of extensions 138 are each disposed in one of holes 120 when knob 128 is in the second configuration.

In some embodiments, knob 128 is fixed relative to emitter 92 and sleeve 34 along axis X1 as knob 128 moves between the first and second configurations. That is, shaft 80 does not translate relative to emitter 92 or sleeve 34 along axis X1 as knob 128 moves between the first and second configurations. In some embodiments, tip 126 extends through opening 46 when knob 128 is in the first configuration and the second configuration. In some embodiments, moving knob 128 between the first configuration and the second configuration does nothing to move tip 126 through opening 46. Rather, tip 126 extends through opening 46 upon assembly of shaft 80 and knob 128 with emitter 92 and sleeve 34. That is, tip 126 extends through opening 46 when instrument is fully assembled, regardless whether knob 128 is in the first configuration or the second configuration.

Tip 126 includes a mating surface, such as, for example, a threaded outer surface 172 configured to engage a mating surface of an implant, such as, for example, implant 174 to couple instrument 32 to implant 174 such that implant 174 can be delivered to a target surgical site using instrument 32, as discussed herein. Implant 174 includes a posterior surface 176 and an anterior surface 178 opposite surface 176. Implant 174 includes a cavity 180 and a cavity 182 that is spaced apart from cavity 180. Cavities 180, 182 each extend into surface 178. In some embodiments, at least a portion of cavity 180 is defined by a mating surface, such as, for example, a threaded inner surface 184, as shown in FIG. 14. In some embodiments, at least a portion of cavity 182 is defined by a mating surface, such as, for example, a threaded inner surface 185, as shown in FIG. 15. Surfaces 184, 185 are each configured to mate with surface 172 to couple implant 174 to instrument 32, as discussed herein. Implant 174 includes screw holes 186, 188 that are accessible when peg 68 is inserted into cavity 180 or cavity 182 such that a fastener, such as, for example, a screw can be inserted into and/or removed from hole 186 and a fastener, such as, for example, a screw can be inserted into and/or removed from hole 188 when peg 68 is inserted into cavity 180 or cavity 182.

In assembly, operation and use, surgical system 30, similar to the systems and methods described herein, is employed with a surgical procedure for treatment of a spinal disorder affecting a section of a spine of a patient, as discussed herein. The components of surgical system 30 are employed with a surgical procedure for treatment of a condition or injury of an affected section of the spine, such as, for example, vertebrae.

In use, to treat a selected section of vertebrae, a medical practitioner obtains access to a surgical site in any appropriate manner, such as through incision and retraction of tissues. In some embodiments, surgical system 30 can be used in any existing surgical method or technique including open surgery, mini-open surgery, minimally invasive surgery and percutaneous surgical implantation, whereby vertebrae are accessed through a mini-incision, or sleeve that provides a protected passageway to the area. Once access to the surgical site is obtained, the particular surgical procedure can be performed for treating the spine disorder.

An incision is made in the body of a patient and a cutting instrument creates a surgical pathway for implantation of components of surgical system 30. A preparation instrument can be employed to prepare tissue surfaces of vertebrae as well as for aspiration and irrigation of a surgical region. Instrument 32 is coupled to an implant, such as, for example, implant 174, that is configured to be inserted into a target site, such as, for example, an intervertebral space between a first vertebra and a second vertebra.

In one embodiment, instrument 32 is used to insert implant 174 in connection with an Anterior Lumbar Interbody Fusion (ALIF) procedure wherein implant 174 is connected to instrument 32 by inserting peg 68 into cavity 182 such that opening 46 is aligned with cavity 180, as shown in FIG. 14. Knob 128 in the first configuration when peg 68 is inserted into cavity 180 such that knob 128 is able to rotate relative to sleeve 34 about axis X1. Knob 128 is rotated about axis X1 in a first rotational direction, such as, for example, clockwise such that threaded outer surface 172 mates with threaded inner surface 184. When threaded outer surface 172 mates with threaded inner surface 184, further rotation of knob 128 relative to sleeve 34 in the first rotational direction causes sleeve 34 and shaft 80 to simultaneously translate axially relative to implant 174 such that implant 174 is drawn toward instrument 32, or vice versa, and surface 62 directly engages surface 178. In some embodiments, knob 128 is rotated relative to sleeve 34 in the first rotational direction until knob 128 moves from the first configuration to the second configuration. When knob 128 is in the second configuration, implant 174 is fixed to instrument 32 and is ready for delivery to the target site by manipulating instrument 32. For example, in some embodiments, implant 174 is guided into an intervertebral space using instrument 32. Once implant 174 is selectively positioned within the intervertebral space, knob 128 is rotated relative to sleeve 32 about axis X1 in a second rotational direction, such as, for example, counterclockwise to uncouple threaded outer surface 172 from threaded inner surface 184. Peg 68 is removed from cavity 182 to disconnect instrument 32 from implant 174 to allow instrument 32 to be removed from the patient, while leaving implant 174 in the intervertebral space.

In one embodiment, instrument 32 is used to insert implant 174 in connection with an Oblique Lateral Interbody Fusion (OLIF) procedure wherein implant 174 is connected to instrument 32 by inserting peg 68 into cavity 180 such that opening 46 is aligned with cavity 182, as shown in FIG. 15. Knob 128 is in the first configuration when peg 68 is inserted into cavity 182 such that knob 128 is able to rotate relative to sleeve 34 about axis X1. Knob 128 is rotated about axis X1 in a first rotational direction, such as, for example, clockwise such that threaded outer surface 172 mates with threaded inner surface 185. When threaded outer surface 172 mates with threaded inner surface 185, further rotation of knob 128 relative to sleeve 34 in the first rotational direction causes sleeve 34 and shaft 80 to simultaneously translate axially relative to implant 174 such that implant 174 is drawn toward instrument 32 and surface 62 directly engages surface 178. In some embodiments, knob 128 is rotated relative to sleeve 34 in the first rotational direction until knob 128 moves from the first configuration to the second configuration. When knob 128 is in the second configuration, implant 174 is fixed to instrument 32 and is ready for delivery to the target site by manipulating instrument 32. For example, in some embodiments, implant 174 is guided into an intervertebral space using instrument 32. Once implant 174 is selectively positioned within the intervertebral space, knob 128 is rotated relative to sleeve 32 about axis X1 in a second rotational direction, such as, for example, counterclockwise to uncouple threaded outer surface 172 from threaded inner surface 185. Peg 68 is removed from cavity 180 to disconnect instrument 32 from implant 174 to allow instrument 32 to be removed from the patient, while leaving implant 174 in the intervertebral space. In some embodiments, the OLIF procedure is an Oblique Lateral Interbody Fusion at L5-S1 (OLIF 5-1) or an approach for Oblique Lateral Interbody Fusion at L2-L5 (OLIF 2-5).

Upon completion of a procedure, as described herein, the surgical instruments, assemblies and non-implanted components of surgical system 30 are removed and the incision(s) are closed. One or more of the components surgical system 30 can be made of radiolucent materials such as polymers. Radiomarkers may be included for identification under x-ray, fluoroscopy, CT or other imaging techniques. In some embodiments, surgical system 100 may include one or a plurality of spinal rods, plates, connectors and/or bone fasteners for use with a single vertebral level or a plurality of vertebral levels.

In some embodiments, one or more bone screws, as described herein, may be engaged with tissue in various orientations, such as, for example, series, parallel, offset, staggered and/or alternate vertebral levels. In some embodiments, one or more of the bone screws may comprise multi-axial screws, sagittal adjusting screws, pedicle screws, mono-axial screws, uni-planar screws, facet screws, fixed screws, tissue penetrating screws, conventional screws, expanding screws, wedges, anchors, buttons, clips, snaps, friction fittings, compressive fittings, expanding rivets, staples, nails, adhesives, posts, fixation plates and/or posts.

In one embodiment, surgical system 30 includes an agent, which may be disposed, packed, coated or layered within, on or about the components and/or surfaces of surgical system 30. In some embodiments, the agent may include bone growth promoting material, such as, for example, bone graft to enhance fixation of the components and/or surfaces of surgical system 30 with vertebrae. In some embodiments, the agent may include one or a plurality of therapeutic agents and/or pharmacological agents for release, including sustained release, to treat, for example, pain, inflammation and degeneration.

It should be appreciated that instrument 32 can be used to insert other implants, in addition to implant 174, for use in a variety of techniques, such as, for example, ALIF, OLIF 5-1, OLIF 2-5 and Direct Lateral Interbody Fusion (DLIF). However, it is envisioned that instrument 32 can be connected to a variety of implants that are the same or similar to implant 174 for use in a variety of different procedures and/or approaches.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical instrument comprising:
   a sleeve extending between opposite proximal and distal ends, the sleeve comprising an inner surface defining a passageway, the proximal end comprising an aperture extending through an outer surface of the sleeve, the distal end comprising an engagement surface and an opening extending through the engagement surface, the opening being in communication with the passageway;
   a member movably disposed in the aperture, the member comprising a spring and a body, the body defining a bore;
   a shaft extending between opposite proximal and distal ends, the proximal end of the shaft extending through the bore, the distal end of the shaft extending through the opening;
   a part coupled to the proximal end of the sleeve, the part comprising a plurality of first holes; and
   a knob comprising a hub having a plurality of second holes, the hub being coupled to the proximal end of the shaft, the knob comprising an insert movably disposed in the hub and a plurality of extensions positioned between the insert and the hub,
   wherein the knob is rotatable between a first configuration in which the extensions are spaced apart from the first holes and a second configuration in which the extensions are disposed in the first holes, the knob being rotatable relative to the part when the knob is in the first configuration, the knob resisting rotation relative to the part when the knob is in the second configuration.

2. The surgical instrument recited in claim 1, wherein:
   the sleeve extends along a first longitudinal axis from the proximal end of the sleeve to the distal end of the sleeve;
   the shaft extends along a second longitudinal axis from the proximal end of the shaft to the distal end of the shaft; and
   the member is configured to move the shaft relative to the sleeve between a first orientation in which the second longitudinal axis is coaxial with the first longitudinal axis and a second orientation in which the second longitudinal axis is offset from the first longitudinal axis.

3. The surgical instrument recited in claim 2, wherein the spring biases the shaft to the second orientation.

4. The surgical instrument recited in claim 2, wherein the spring moves along an axis that is perpendicular to the first and second longitudinal axis as the shaft moves between the first orientation and the second orientation.

5. The surgical instrument recited in claim 1, wherein:
   the sleeve extends along a first longitudinal axis from the proximal end of the sleeve to the distal end of the sleeve;
   the shaft extends along a second longitudinal axis from the proximal end of the shaft to the distal end of the shaft; and
   the spring biases the body such that the second longitudinal axis is offset from the first longitudinal axis.

6. The surgical instrument recited in claim 1, wherein the inner surface is a first inner surface, the spring comprising a first end that directly engages a second inner surface of the sleeve and an opposite second end that directly engages the body, the second inner surface being positioned between the first inner surface and the outer surface.

7. The surgical instrument recited in claim 1, wherein the body is cylindrical.

8. The surgical instrument recited in claim 1, wherein the distal end of the sleeve comprises a peg extending outwardly from the engagement surface.

9. The surgical instrument recited in claim 1, wherein the shaft is rotatable relative to the sleeve when the knob is in the first configuration and the shaft resists rotation relative to the sleeve when the knob is in the second configuration.

10. The surgical instrument recited in claim 1, further comprising springs, wherein the knob is biased to the second orientation by the springs.

11. The surgical instrument recited in claim 1, wherein the hub comprises a threaded inner surface that directly engages a threaded outer surface of the insert to couple the insert to the hub.

12. The surgical instrument recited in claim 1, wherein:
the second holes are offset from each of the first holes when the knob is in the first configuration; and
each of the second holes is aligned with one of the first holes when the knob is in the second configuration.

13. A surgical instrument comprising:
a sleeve extending between opposite proximal and distal ends, the sleeve comprising an inner surface defining a passageway;
a part coupled to the proximal end of the sleeve, the part comprising a plurality of first holes and an inner surface defining a channel;
a shaft extending between opposite proximal and distal ends, the distal end of the shaft being positioned in the passageway and the channel; and
a knob coupled to the proximal end of the shaft, the knob comprising a hub having a plurality of second holes, the knob comprising an insert disposed in the hub and a plurality of extensions positioned between the insert and the hub,
wherein the knob is rotatable between a first configuration in which the extensions are spaced apart from the first holes and a second configuration in which the extensions are disposed in the first holes, the knob being rotatable relative to the part when the knob is in the first configuration, the knob resisting rotation relative to the part when the knob is in the second configuration.

14. The surgical instrument recited in claim 13, wherein:
the shaft extends along a longitudinal axis from the proximal end of the shaft to the distal end of the shaft; and
the insert is fixed relative to the hub along the longitudinal axis as the knob moves between the first configuration and the second configuration.

15. The surgical instrument recited in claim 13, wherein:
the second holes are offset from each of the first holes when the knob is in the first configuration; and
each of the second holes is aligned with one of the first holes when the knob is in the second configuration.

16. The surgical instrument recited in claim 13, wherein:
the shaft extends along a longitudinal axis from the proximal end of the shaft to the distal end of the shaft;
the hub comprises a plate extending perpendicular to the longitudinal axis, the second holes extending through the plate;
tips of the extensions are flush with a distal surface of the plate when the knob is in the first configuration; and
tips of the extensions are distal to the distal surface when the knob is in the second configuration.

17. The surgical instrument recited in claim 13, wherein:
the proximal end of the sleeve includes an aperture extending into an outer surface of the sleeve; and
the surgical instrument further comprises a member movably disposed in the aperture, the member comprising a spring and a body, the body defining a bore, the distal end of the shaft extending through the bore; and
the member is configured to move the shaft relative to the sleeve between a first orientation in which the shaft is coaxial with the sleeve and a second orientation in which the shaft is not coaxial with the sleeve.

18. The surgical instrument recited in claim 13, wherein:
the sleeve comprises a circumferential flange; and
the part comprises a body and a pair of arms that are pivotable relative to the body and configured to engage the flange to couple the part to the sleeve.

19. The surgical instrument recited in claim 13, wherein the part comprises an emitter configured to generate a signal representative of the position of the surgical instrument.

20. A surgical instrument comprising:
a sleeve extending along a first longitudinal axis between opposite proximal and distal ends, the sleeve comprising a first inner surface defining a passageway, the proximal end comprising an aperture extending through the first inner surface and an outer surface of the sleeve and into a second inner surface of the sleeve, the distal end comprising an engagement surface and an opening extending through the engagement surface, the opening being in communication with the passageway, the distal end comprising a peg extending outwardly from the engagement surface, the sleeve comprising a circumferential flange;
an emitter configured to generate a signal representative of the position of the surgical instrument, the emitter being coupled to the proximal end of the sleeve, the emitter comprising a plurality of first holes and an inner surface defining a channel, the emitter comprising a body and a pair of arms that are pivotable relative to the body and configured to engage the flange to couple the emitter to the sleeve;
a member movably disposed in the aperture, the member comprising a spring and a cylindrical body, the cylindrical body defining a bore, the spring comprising a first end that directly engages the second inner surface and an opposite second end that directly engages the cylindrical body;
a shaft extending along a second longitudinal axis between opposite proximal and distal ends, the proximal end of the shaft extending through the bore and the channel, the distal end of the shaft extending through the opening; and
a knob coupled to the proximal end of the shaft, the knob comprising a hub having a plurality of second holes, the knob comprising an insert disposed in the hub and a plurality of extensions positioned between the insert and the hub, the knob comprising a plurality of springs that are each positioned between the insert and one of the extensions, the hub comprising a threaded inner surface that directly engages a threaded outer surface of the insert to couple the insert to the hub,
wherein the member is configured to move the shaft relative to the sleeve between a first orientation in which the second longitudinal axis is coaxial with the first longitudinal axis and a second orientation in which the second longitudinal axis is offset from the first longitudinal axis, and
wherein the knob is rotatable between a first configuration in which the extensions are spaced apart from the first holes and a second configuration in which the extensions are disposed in the first holes, the knob being rotatable relative to the emitter when the knob is in the first configuration, the knob resisting rotation relative to the emitter when the knob is in the second configuration.

* * * * *